US007659828B2

(12) United States Patent
Wehrs et al.

(10) Patent No.: US 7,659,828 B2
(45) Date of Patent: Feb. 9, 2010

(54) INDUSTRIAL FIELD DEVICE WITH AUTOMATIC INDICATION OF SOLIDS

(75) Inventors: David L. Wehrs, Eden Prairie, MN (US); Robert J. Karschnia, Chaska, MN (US); Evren Eryurek, Edina, MN (US)

(73) Assignee: Rosemount Inc., Eden Prairie, MN (US)

( * ) Notice: Subject to any disclaimer, the term of this patent is extended or adjusted under 35 U.S.C. 154(b) by 240 days.

(21) Appl. No.: 11/507,356

(22) Filed: Aug. 21, 2006

(65) Prior Publication Data
US 2007/0069903 A1    Mar. 29, 2007

Related U.S. Application Data

(60) Provisional application No. 60/710,208, filed on Aug. 22, 2005.

(51) Int. Cl.
*G08B 21/00* (2006.01)
(52) U.S. Cl. .................. 340/603; 340/621; 340/632; 340/825.69
(58) Field of Classification Search ........... 340/603, 340/617, 621, 606–612, 614, 618, 626, 632, 340/825.36, 825.46, 825.69; 507/200, 203, 507/252
See application file for complete search history.

(56) References Cited

U.S. PATENT DOCUMENTS

| | | | | |
|---|---|---|---|---|
| 3,816,773 A | * | 6/1974 | Baldwin et al. | 310/319 |
| 3,854,323 A | | 12/1974 | Hearn et al. | 73/61 |
| 4,240,287 A | * | 12/1980 | Mast et al. | 73/61.75 |
| 4,448,062 A | | 5/1984 | Peterson et al. | 73/86 |
| 5,257,530 A | * | 11/1993 | Beattie et al. | 73/61.75 |
| 5,441,110 A | * | 8/1995 | Scott, III | 166/308.1 |
| 5,442,173 A | * | 8/1995 | Wraight | 250/260 |
| 6,192,751 B1 | * | 2/2001 | Stein et al. | 73/290 V |
| 6,484,585 B1 | * | 11/2002 | Sittler et al. | 73/718 |
| 6,520,020 B1 | * | 2/2003 | Lutz et al. | 73/706 |
| 2004/0007059 A1 | | 1/2004 | Tudor | 73/152.42 |
| 2005/0109112 A1 | | 5/2005 | Gysling et al. | 73/587 |

FOREIGN PATENT DOCUMENTS

WO    WO 93/09405    5/1993

OTHER PUBLICATIONS

The International Search Report and Written Opinion from U.S. Appl. No. PCT/US2006/032553, filed Aug. 21, 2006.
"TecWel Well sand detector (WSD)," TecWel AS, 2004, 4 pages.

(Continued)

*Primary Examiner*—Daniel Previl
(74) *Attorney, Agent, or Firm*—Christopher R. Christenson; Westman, Champlin & Kelly, P.A.

(57) ABSTRACT

An industrial field device provides information indicative of a process variable. The field device includes a controller, communication circuitry, a process variable sensor and measurement circuitry. The communication circuitry is coupled to the controller. The process variable sensor has an electrical characteristic that changes based on a variable of a process fluid. The measurement circuitry is coupled to the process variable sensor and coupled to the controller. The controller is configured to generate communication via the communication circuitry relative to the process variable, and to provide an indication of sand flow or other solids in the fluid.

10 Claims, 5 Drawing Sheets

OTHER PUBLICATIONS

"TecWel AS—Acoustic Technology in Wells," Business Briefing: Exploration & Production: The Oil & Gas Review 2004, p. 1-2.

First Communication issued for European patent application No. 06 801 975.1, dated Jan. 21, 2009.

* cited by examiner

INDUSTRIAL FIELD DEVICE WITH AUTOMATIC INDICATION OF SOLIDS

CROSS-REFERENCE TO RELATED APPLICATION

The present application is based on and claims the benefit of U.S. provisional patent application Ser. No. 60/710,208, filed Aug. 22, 2005, the content of which is hereby incorporated by reference in its entirety.

BACKGROUND

During production from a natural gas or oil well, it is not uncommon to hit pockets of fluid with significant sand content. Sand is highly undesirable for a number of reasons. Sand can fill the bore of the well; sand can fill the process system; or sand can simply diminish productivity of the well and/or production operation. Further, sand can cause undesirable wear of piping components, especially at elbows, or restrictions, as well as valves and differential pressure producers, such as orifice plates, venturies, or v-cones. Thus, the presence of sand during production from a natural gas or oil well can lead to pipe and valve erosion as well as the potential of failure of a variety of equipment used during production. Further still, sand flow can generate calibration shifts in the differential producers. Thus, it is very important during production from a natural gas or oil well that any sand flow be detected substantially immediately such that the problem can be addressed quickly and effectively, either locally at the production site, or remotely. This remedy may sometimes involve temporary shutting down the well, making adjustments to the well head operation, or changes to the well or field management (changes in injection, well depth, et cetera).

When the solids, entrained in the fluid, impinge upon production machinery, such as piping, valves, differential producers, et cetera, the impingement generates a sound. Generally the solids are sand and the fluid is a hydrocarbon fluid. However, other examples of solids entrained in fluid include slurries such as pulp stock, mining slurries, dredging slurries and sewage. It is known to sense sand in hydrocarbon production systems using acoustic sensors. Such sensors are generally dedicated devices that are tuned to the general frequency band within which the impingement's acoustic energy falls. While such devices are useful, they provide added complexity and costs to the overall production operation. Additionally, even state-of-the-art acoustic well sound detectors do not provide signaling that is easily integrated into an overall process measurement and control system.

SUMMARY

An industrial field device provides information indicative of a process variable. The field device includes a controller, communication circuitry, a process variable sensor and measurement circuitry. The communication circuitry is coupled to the controller. The process variable sensor has an electrical characteristic that changes based on a variable of a process fluid. The measurement circuitry is coupled to the process variable sensor and coupled to the controller. The controller is configured to generate communication via the communication circuitry relative to the process variable, and to provide an indication of sand flow.

DETAILED DESCRIPTION OF ILLUSTRATIVE EMBODIMENTS

Industrial field devices such as pressure transmitters are common devices in any natural gas or oil well production installation. Gauge pressure transmitters are used to monitor well head pressure, as well as operation around separators and down-hole pressure. Differential pressure transmitters are used with the differential producers mentioned above to measure the flow rate of the produced oil or gas. Another type of industrial field device is known as process fluid flow meter. Examples of process fluid flow meters include vortex meters and Coriolis meters.

Industrial field devices are very common and generally have the ability to communicate additional information via digital communication protocols such as the Highway Addressable Remote Transducer (HART®) protocol, or the FOUNDATION™ Fieldbus protocol via wired process communication connections, or via wireless techniques. In accordance with embodiments of the present invention, industrial field devices, such as process pressure transmitters or flow meters are adapted to not only sense their primary process variable, but also sense the presence of sand during production from a natural gas or oil well. This dual role provides an important synergy in that the overall complexity and costs of the physical system can be reduced, and the sand detection signal can be easily integrated into known process communication regimes.

Figure 1:
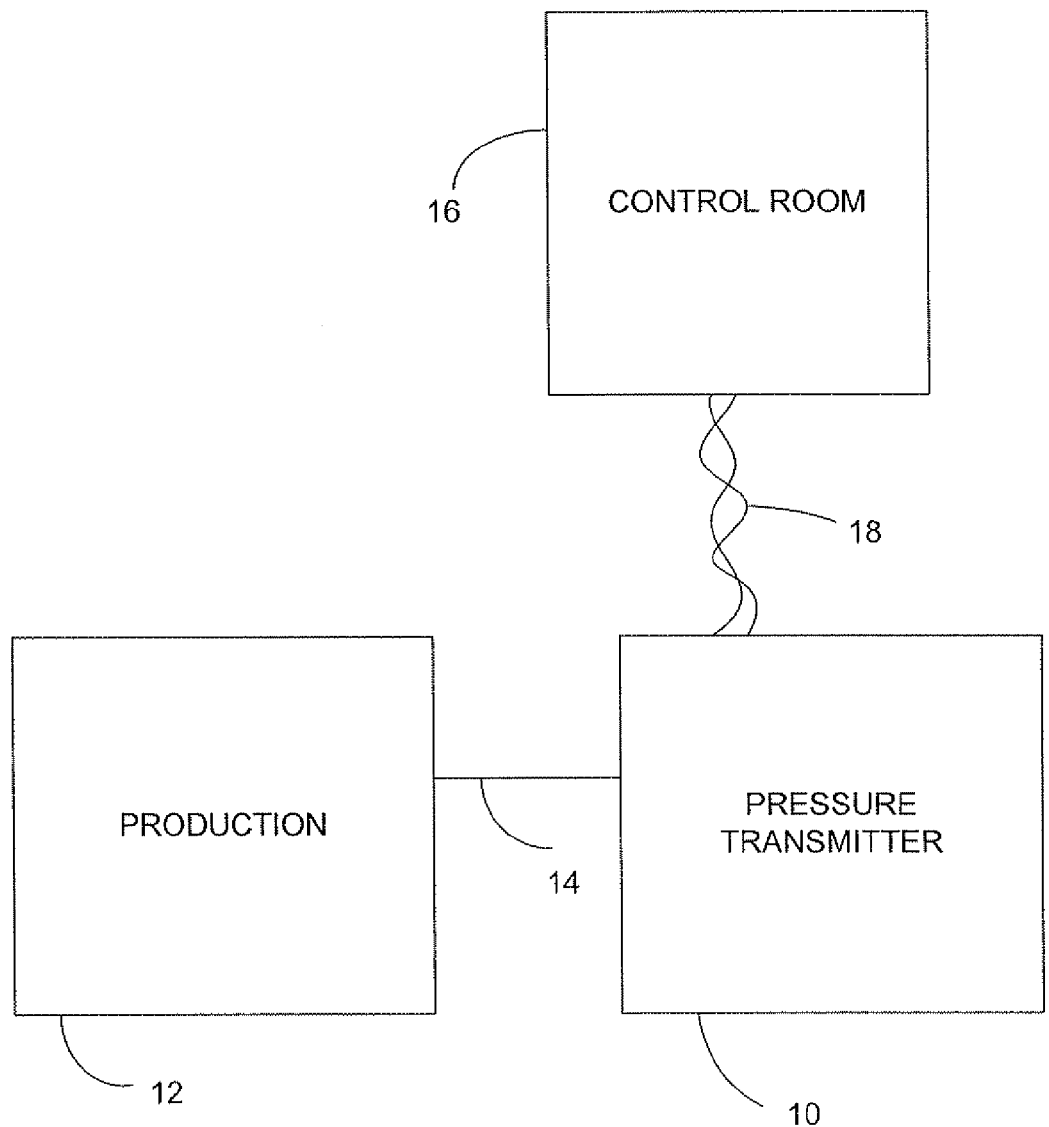
FIG. 1 is a diagrammatic view of a process measurement system in which embodiments of the present invention are particularly useful.

FIG. 1 is a diagrammatic view of a process control system for natural gas and/or oil well production with which embodiments of the present invention are particularly useful. FIG. 1 illustrates process pressure transmitter 10 operably coupled to a natural gas or oil well production process illustrated diagrammatically as box 12. In reality, production 12 may include a vast number of pieces of industrial machinery disposed over a relatively large area, on the order of acres. FIG. 1 illustrates pressure transmitter 10 operably coupled, by way of line 14, to natural gas/oil production 12. Typically, a pressure transmitter is physically disposed upon, or proximate, piping that conveys the natural gas or oil fluid. However, any suitable coupling can be used. Pressure transmitter 10 is electrically coupled to control room 16 via process communication loop 18. Control room 16 may also be coupled to a number of other process devices such as process variable transmitters, process actuators, or any other suitable devices.

Figure 2:
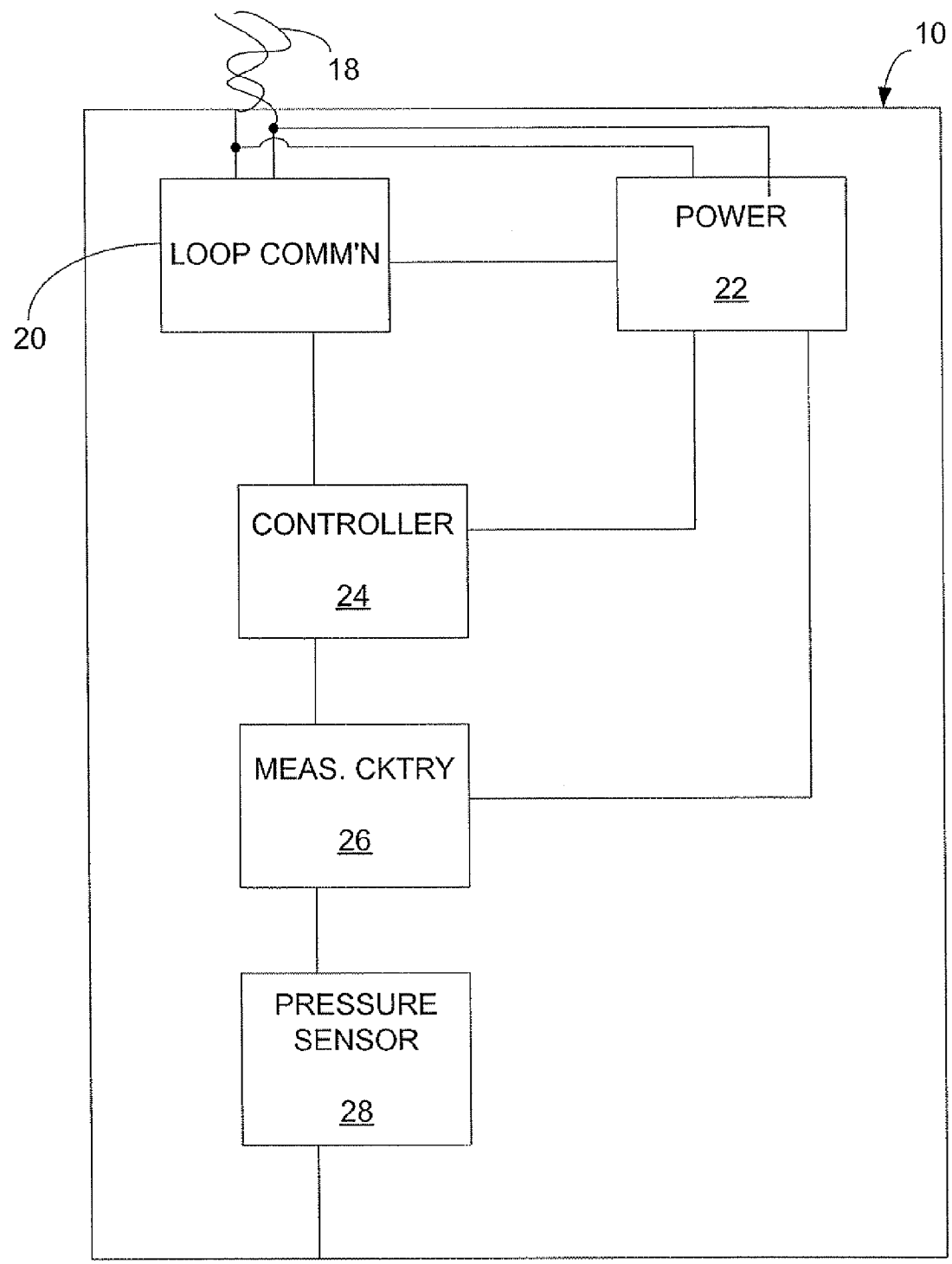
FIG. 2 is a diagrammatic view of a process pressure transmitter configured to detect sand flow in accordance with an embodiment of the present invention.

FIG. 2 is a diagrammatic view of process pressure transmitter 10 with which embodiments of the present invention are useful. Transmitter 10 includes loop communication module 20, power module 22, controller 24, measurement circuitry 26, and pressure sensor 28. Loop communication circuitry is operably coupleable to process communication loop 18 and is configured for communication in accordance with an industry standard communication protocol. Examples of suitable industry standard communication protocols include, but are not limited to, HART®, FOUNDATION™ Fieldbus, Profibus-PA and Controller Area Network (CAN). A number of process communication loops are known to have the ability to provide operating power to attached process devices. As such, power module 22, in accordance with known techniques, is operably coupleable to process communication loop 18 and derives operating power for transmitter 10 from energy provided over the communication loop. As indicated in FIG. 2, power module 22 is operably coupled to loop communication module 20, controller 24 and measurement circuitry 26.

Controller 24 is operably coupled to loop communication module 20 and measurement circuitry 26. Controller 24, which is preferably a low-power microprocessor, provides transmitter 10 with the ability to execute a number of sophisticated analyses. Thus, while transmitter 10 may provide a process pressure output, like prior art transmitters, it may also provide an indication of solids, such as sand, impinging upon surfaces near pressure transmitter 10. The actual ways in which controller 24 can detect sand impingement will be described in greater detail below. Controller 24 may include, or be coupled to, any suitable forms of memory including non-volatile memory and/or volatile memory. Additionally, instructions stored on suitable memory can cause controller 24 to execute digital signal processing algorithms that help detect sand flow.

Measurement circuitry 26 is operably coupled to pressure sensor 28 and to controller 24. Measurement circuitry 26 preferably includes an analog-to-digital converter. In one embodiment, the analog-to-digital converter is known as a Sigma-Delta analog-to-digital converter providing 22 conversions per second. In this embodiment, each converted digital representation of the process pressure becomes a data point for digital signal processing. For example, a Fast Fourier Transform (FFT) is applied to the digital process data points to generate information indicative of the presence of sand flow. An example of a suitable analysis can include power spectral density (PSD) analysis that operates using a known analog-to-digital converter operating in a known manner. In this regard, at least one embodiment of the present invention can be implemented wholly in software within pressure transmitter 10. Thus, embodiments of the present invention can be applied to process variable transmitters that are currently installed in the field, or already manufactured, without having to modify their circuitry.

Sigma-Delta converters are often used in the process measurement and control industry due to their fast conversion times and high accuracy. Sigma-Delta converters generally employ an internal capacitor charge pumping scheme that generates a digital bit stream that is analyzed, generally by counting positive 1's over a set interval. For example one Sigma-Delta converter currently in use provides a bit stream signal consisting of 50% 1's to indicate the minimum pressure measurement, and 75% 1's to indicate the maximum pressure measurement. The digital bit stream is filtered to remove or attenuate fluctuating components prior to determination of the process variable. The filter data is then used with well known equations to calculate the process variable.

In accordance with another embodiment of the present invention, the digital bit stream within the analog-to-digital converter is used directly for digital signal processing, such as power spectral density analysis. This bit stream usually has a frequency that is many orders of magnitude higher than the conversion frequency. For example, a known Sigma-Delta converter provides a digital bit stream that has a frequency of approximately 57 kHz. While those skilled in the art will recognize many ways in which PSD analysis can be performed upon the digital bit stream, one suitable method follows. For a given interval, such as 10 seconds, digital data from the bit stream is collected and saved. In the example above, 10 seconds of 57 kHz data yields 570,000 stored bits. The DC component can be optionally removed from the stored data by subtracting the average bit value (number of 1's divided by the total number of bits) from each stored bit. Next, power spectral density is computed on the adjusted data. This is preferably done using a 65536 point FFT and a Hanning window size of 65536. The size of the FFT was chosen because it is the power of two closest to the sampling bit frequency, and given a duration of 10 seconds, it provides acceptable averaging of the spectrum. However, other sizes may be used in accordance with embodiments of the present invention.

Pressure sensor 28 is a known device that has an electrical characteristic, such as capacitance, that varies with applied pressure. Generally, a pressure sensor, such as pressure sensor 28 is fluidically coupled to a source of process pressure by way of isolation fluid. However, it is known to directly couple a process pressure to a pressure sensor. Many types of pressure sensors are known. One such type utilizes a conductive deflectable diagram spanning an separating a chamber filled with dielectric fluid. The dielectric fluid on each side of the deflectable diagram is operably coupled to a source of pressure. One or more electrodes within the pressure sensor form a variable capacitor with the deflectable diagram. As pressure changes and the diagram deflects, the capacitance varies accordingly.

Another type of known pressure sensor is the semiconductor-based pressure sensor. These types of pressure sensors are taught in U.S. Pat. No. 5,637,802, assigned to the Assignee of the present invention. Such semiconductor-based pressure sensors generally provide a capacitance that varies with the deflection of a portion of the semiconductor sensor. The deflection is in response to an applied pressure. Semiconductor-based sensors have very favorable hysteresis and have an extremely high frequency response. Additional information related to semiconductor-based pressure sensors can be found in U.S. Pat. Nos. 6,079,276; 6,082,199; 6,089,907; 6,484,585; and 6,520,020, all of which are assigned to the Assignee of the present invention. In this embodiment, the use of a semiconductor-based pressure sensor for pressure sensor 28 in combination with the bit stream analysis listed above with respect to measurement circuitry provide the ability to determine, or otherwise detect, the presence of solids flowing in the process fluid based upon analysis of relatively high-frequency signals, that would otherwise simply be discarded in normal process variable calculations.

Figure 3:
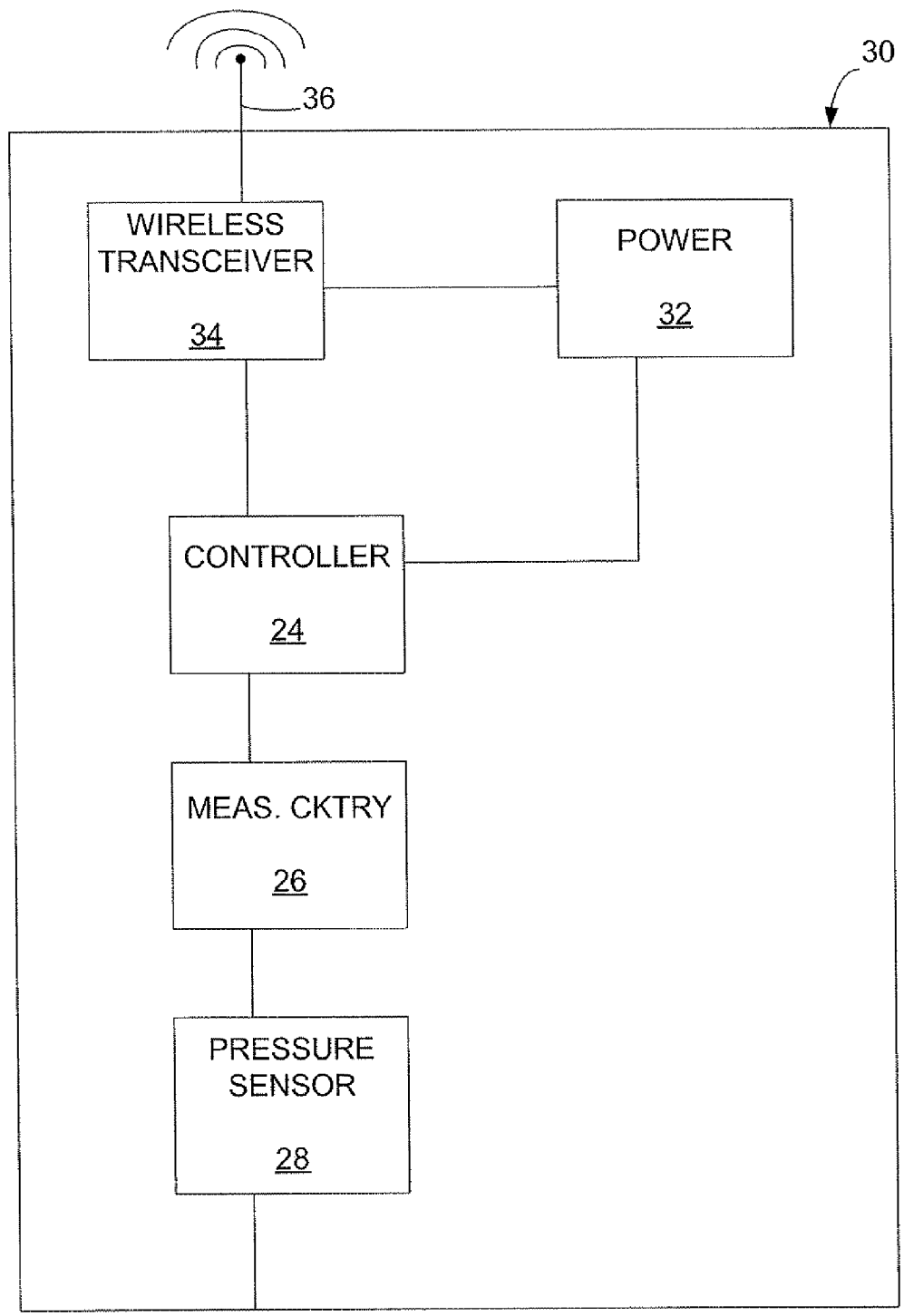
FIG. 3 is a diagrammatic view of a process pressure transmitter configured to detect sand flow in accordance with another embodiment of the present invention.

FIG. 3 is a diagrammatic view of a process pressure transmitter 30 with which embodiments of the present invention can be practiced. Some components of pressure transmitter 30 are similar to components of pressure transmitter 10, and like components are numbered similarly. The biggest difference between pressure transmitter 30 and pressure transmitter 10 is that pressure transmitter 30 operates as a wireless device. Accordingly, power module 32 of pressure transmitter 30 generally includes an energy cell, such as a battery, or capacitor that may be operably coupled, either continuously or periodically to a recharging source, such as a solar panel. In place of loop communication module 20, wireless pressure transmitter 30 includes wireless transceiver 34. Wireless transceiver 34 is operably coupled to controller 24 and receives electrical power from power module 32. Wireless transceiver 34 is coupled to controller 24 and interacts with external wireless devices via antenna 36 based upon commands and/or data from controller 24. Depending on the application, wireless transceiver 34 may be adapted to communicate in accordance with any suitable wireless communication protocol including, but not limited to: wireless networking technologies (such as IEEE 802.11b Wireless Access Points and Wireless Networking Devices Built by Linksys, of Irvine, Calif.), cellular or digital networking technologies (such as Microburst® by Aeris Communications Inc. of San Jose, Calif.), ultra wide band, free optics, global system for mobile communications (GSM), general packet radio service (GPRS), code division multiple access (CDMA), spread spectrum technology, infrared communications techniques, SMS (short messaging service/text messaging) or any other suitable wireless technology. Further, known data collision technology can be used such that multiple transmitters 30 can coexist within wireless operating range of one another. Such collision prevention can include using a number of different radio-frequency channels and/or spread spectrum techniques. Wireless transceiver 34 can also be used with pressure transmitter 10 thereby providing wireless communication abilities to pressure transmitter 10. In that regard, pressure transmitter 10 may provide process variable information over the wired process communication loop, but provide sand flow detection information via wireless communication.

Figure 4:
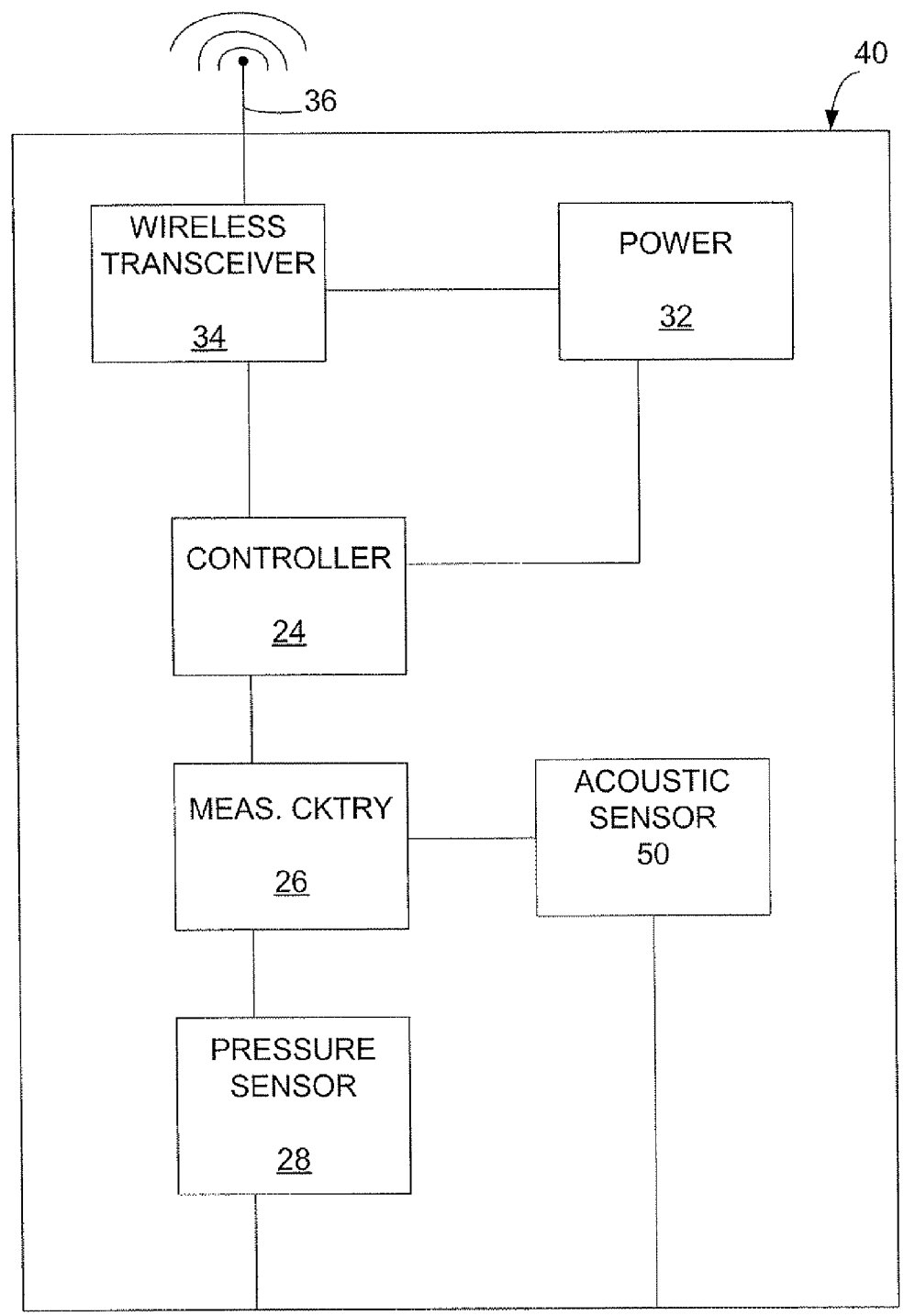
FIG. 4 is a diagrammatic view of a process pressure transmitter configured to detect sand flow in accordance with another embodiment of the present invention.

FIG. 4 is a diagrammatic view of a process pressure transmitter 40 in accordance with an embodiment of the present invention. Some components of pressure transmitter 40 are similar to components of pressure transmitter 30, and like components are numbered similarly. Pressure transmitter 40 includes acoustic sensor 50 coupled to measurement circuitry 26. While sensor 50 is illustrated as a component of transmitter 40, sensor 50 could in fact be disposed remotely from transmitter 40, such as mounted on a pipe, and electrically coupled to measurement circuitry 26 through suitable cabling. Sensor 50 can be any suitable sensor such as a piezoelectric transducer or microphone. Moreover, the signal processing techniques described with respect to embodiments of the present invention can be applied to the signals from sensor 50 as well.

As set forth above, the impingement of solids, such as sand, on elbows, constrictions, or differential producers within the process piping creates acoustic energy that is conducted via the piping and the fluid up and down the pipe from the impact point(s). This acoustic energy is detected by a pressure transmitter configured in accordance with any of the various configurations set forth above. The acoustic energy can generally be detected by one or more of the following three methods.

The sand's noise signal is additive to the gauge or differential pressure signal, creating higher variability in the measured pressure signal. This increase in variability can be detected by monitoring the variability in real time. If the variability of the measured pressure signal exceeds a pre-selected value, sand flow is deemed detected. Known statistical process monitoring techniques generally involve the characterization of the signal by filtering and calculation of the mean and standard deviation of the process pressure. Filtering is often required (such as high pass filtering) to remove the slower changes in the signal, such as those due to changes in well head operation. If the value of the standard deviation is above a pre-selected value, an alarm is generated and sent to the local or remote operator via any suitable means including analog and/or digital communication. Alternately, a PlantWeb® alert or other alarm indication can be generated and sent to the local or remote operator via digital communications. To maximize the value of such calculations, it is preferred that the process pressure transmitter have a good frequency response and a relatively high update rate. The 22 Hz update rate listed above is standard for a pressure transmitter such as the model 3051S or 3051C sold by Rosemount Inc., of Chanhassen, Minn., and such update rate is believed to be sufficient for accurate detection of the acoustic signal.

Yet another manner in which detection can be effected relates to digital signal processing. The acoustic signal created by the sand flow results in a significant increase in noise at a particular frequency or range of frequencies that can be measured by the pressure transmitter via traditional digital signal processing means. For example, the pressure transmitter, in addition to its normal calculation of pressure, also performs filtering via Finite Impulse Response (FIR) or Infinite Impulse Response (IIR) digital filters over a range of frequencies preferably ranging from 1 Hz to 11 Hz, the Nyquist frequency for the 3051 transmitters listed above. The amplitude of the filtered signals is measured and if the measured amplitude is higher than a preset value, an alarm or PlantWeb® alert is generated to the local or remote operator.

Still another manner in which sand flow can be detected is by utilizing any of the high-frequency measurement techniques disclosed above. The 3051 series of pressure transmitters noted above currently use analog-to-digital converters based on the Sigma-delta technology. This provides a technique whereby the signal can be sampled at a significantly higher rate, such as 50 kHz using a one bit A/D converter and down sampled and filtered to produce significantly higher resolution at a lower update rate (i.e., 24 bits or higher at 22 Hz). This technique, as applied to pressure measurement is known. Thus, using a high-frequency pressure sensor and/or high-frequency bit stream data from the Sigma-delta converter, useful information about the state of sand flow is determined from the high-frequency signals based upon digital sampling and processing techniques.

Figure 5:
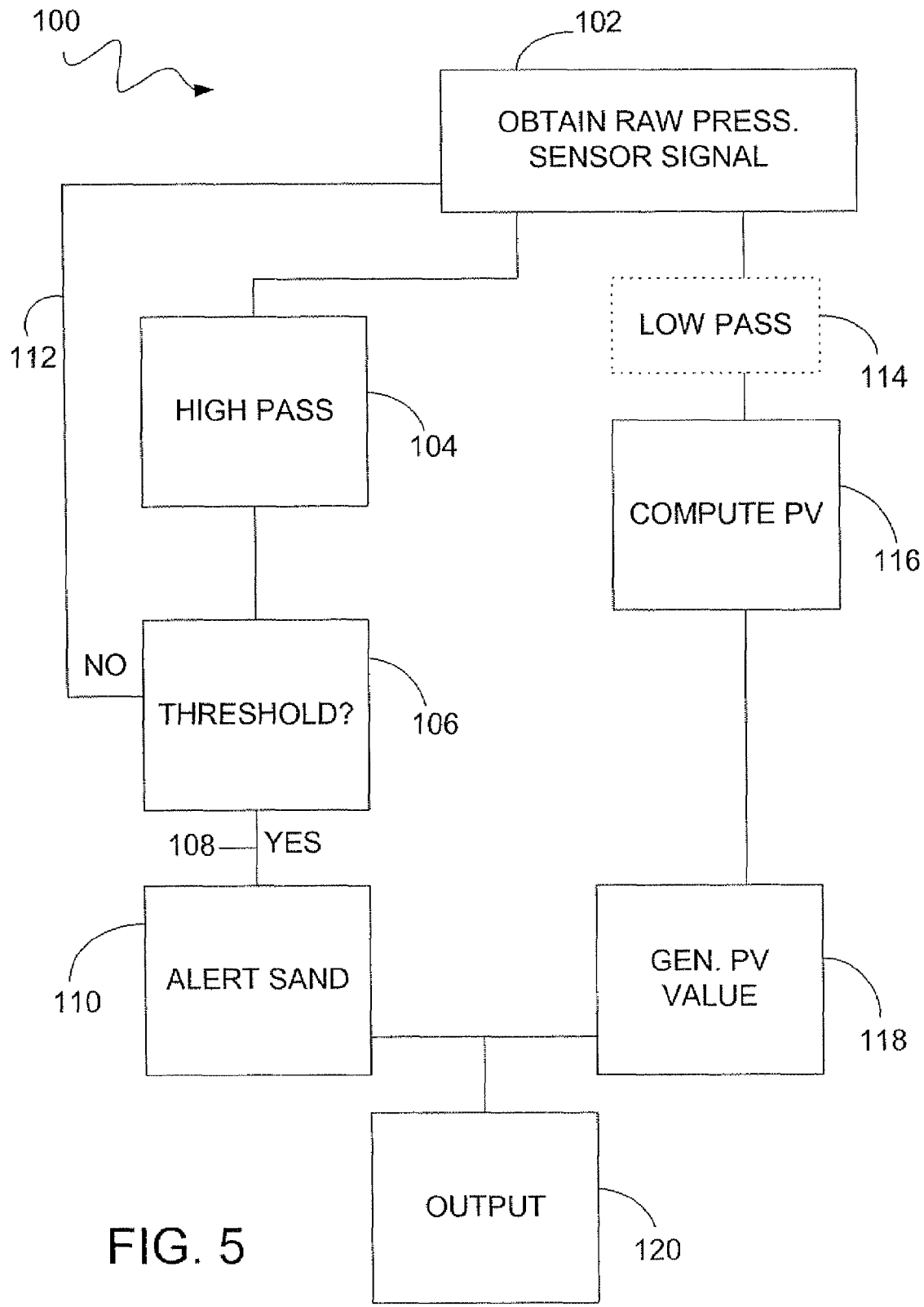
FIG. 5 is a flow diagram of a method of providing a process pressure and sand flow alert in accordance with an embodiment of the present invention.

FIG. 5 is a flow diagram of a method for providing an indication of sand flow in conjunction with a process variable in accordance with an embodiment of the present invention. Method 100 begins at block 102 where raw pressure sensor signal information is obtained. Preferably, this signal information is raw bit stream data from a Sigma-delta analog-to-digital converter. The data can be high pass filtered 104, to remove low-frequency signals and the amplitude of the remainder signal can be compared with a known threshold, as indicated at block 106. If the signal is above the threshold, control passes along block 108 to generate a sand alert as indicated at block 110. However, if the measured signal is less than the threshold, control returns to block 102 along line 112. Additionally, the raw sensor signal can optionally be passed through a low-pass filter, as indicated at phantom block 114. The lower-frequency signal can be used to compute the process pressure as indicated at block 116 in accordance with known techniques. Then, the process pressure value is generated based upon the computed process pressure as indicated at block 118. Finally, at block 120 any alert, as well as process variable information, is output. As set forth above, both such pieces of information can be transmitted digitally upon any suitable process communication loop, or using wireless techniques. Moreover, one piece of information can be transmitted in accordance with one technique, while the other is transmitted differently. Further still, a sand alert can take numerous forms such as not only being transmitted digitally over a process communication loop, but also flashing an enunciator or generating an audible alarm at the process pressure transmitter itself.

Although the present invention has been described with reference to preferred embodiments, workers skilled in the art will recognize that changes may be made in form and detail without departing from the spirit and scope of the invention.

What is claimed is:

1. An industrial field device for providing information indicative of a process variable, the field device including:
   a controller;
   a loop communication module coupled to the controller and configured to communicate process variable information over a process communication loop;
   a process fluid pressure sensor having an electrical characteristic that changes related to a pressure of a process fluid;
   measurement circuitry coupled to the process fluid pressure sensor and coupled to the controller; and
   wherein the controller is configured to generate communication via the loop communication module relative to the process fluid pressure, and wherein the controller is also configured to provide an indication of flow of a solid within the process fluid based upon processing information from the measurement circuitry and determining whether a statistical parameter of the process variable exceeds a pre-selected value.

2. The industrial field device of claim 1, wherein the solid is sand.

3. The industrial field device of claim 1, wherein the pressure sensor is a semiconductor-based pressure sensor.

4. The industrial field device of claim 1, wherein the statistical parameter is variability.

5. The industrial field device of claim 1, wherein the statistical parameter is standard deviation.

6. The industrial field device of claim 1, wherein the loop communication module is coupleable to a wired process communication loop and is configured to communicate in accordance with a process industry standard protocol.

7. The industrial field device of claim 6, and further comprising a power module operably coupleable to the process communication loop, and configured to wholly power the field device with energy received from the process communication loop.

8. An industrial field device for providing information indicative of a process variable, the field device including:
   a controller;
   a loop communication module coupled to the controller and configured to communicate process variable information over a process communication loop;
   a process fluid pressure sensor having an electrical characteristic that changes related to a pressure of a process fluid;
   measurement circuitry coupled to the process fluid pressure sensor and coupled to the controller; and
   wherein the controller is configured to generate communication via the loop communication module relative to the process fluid pressure, and wherein the controller is also configured to provide an indication of flow of a solid within the process fluid based upon processing information from the measurement circuitry by observing an amplitude of a frequency spectrum within which solid impingement is expected.

9. The industrial field device of claim 8, wherein observing an amplitude of the frequency spectrum includes using bit stream data from an analog-to-digital converter.

10. The industrial field device of claim 9, wherein the analog-to-digital converter is a Sigma-Delta analog-to-digital converter.

* * * * *

UNITED STATES PATENT AND TRADEMARK OFFICE
CERTIFICATE OF CORRECTION

PATENT NO. : 7,659,828 B2
APPLICATION NO. : 11/507356
DATED : February 9, 2010
INVENTOR(S) : Wehrs et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 412 days.

Signed and Sealed this

Thirtieth Day of November, 2010

David J. Kappos
*Director of the United States Patent and Trademark Office*